(12) United States Patent
Raines

(10) Patent No.: US 9,737,700 B2
(45) Date of Patent: Aug. 22, 2017

(54) FLEXIBLE MULTI-USE CONTAINER, SYSTEM AND METHOD OF MANUFACTURE

(71) Applicant: B. Braun Medical Inc., Bethlehem, PA (US)

(72) Inventor: Kenneth C. Raines, Bethlehem, PA (US)

(73) Assignee: B. BRAUN MEDICAL INC., Bethlehem, PA (US)

(*) Notice: Subject to any disclaimer, the term of this patent is extended or adjusted under 35 U.S.C. 154(b) by 293 days.

(21) Appl. No.: 14/627,392

(22) Filed: Feb. 20, 2015

(65) Prior Publication Data

US 2015/0238749 A1 Aug. 27, 2015

Related U.S. Application Data

(60) Provisional application No. 61/943,023, filed on Feb. 21, 2014.

(51) Int. Cl.
| | |
|---|---|
| *A61M 39/22* | (2006.01) |
| *A61M 39/24* | (2006.01) |
| *A61M 39/26* | (2006.01) |
| *A61J 1/14* | (2006.01) |
| *A61M 39/02* | (2006.01) |
| *A61M 39/10* | (2006.01) |
| *A61J 1/10* | (2006.01) |

(52) U.S. Cl.
CPC ............ *A61M 39/22* (2013.01); *A61J 1/1406* (2013.01); *A61J 1/1481* (2015.05); *A61M 39/24* (2013.01); *A61M 39/26* (2013.01); *A61J 1/10* (2013.01); *A61M 2039/0205* (2013.01); *A61M 2039/1072* (2013.01); *A61M 2039/1077* (2013.01); *A61M 2039/2433* (2013.01); *A61M 2039/2473* (2013.01)

(58) Field of Classification Search
CPC .. A61J 1/10; A61J 1/1406; A61M 2039/2433; A61M 2039/1072; A61M 39/24
See application file for complete search history.

(56) References Cited

U.S. PATENT DOCUMENTS

| | | | | |
|---|---|---|---|---|
| 5,578,059 | A * | 11/1996 | Patzer | ............... A61M 39/045 251/149.1 |
| 5,928,213 | A * | 7/1999 | Barney | ................... A61J 1/10 206/219 |
| 8,647,310 | B2 * | 2/2014 | Fangrow, Jr. | ......... A61M 39/26 251/149.2 |
| 8,679,090 | B2 * | 3/2014 | Anderson | ............ A61M 39/26 604/246 |

* cited by examiner

*Primary Examiner* — Leslie Deak
(74) *Attorney, Agent, or Firm* — Kenealy Vaidya LLP

(57) ABSTRACT

The disclosed embodiments provide a valve structure that is hermetically sealed to a lower flange formed on an IV bag to form a one-way outlet accessible with a luer tip syringe that does not have a needle. The valve structure can include a piston in combination with a disc or disc valve. The piston can have a slit septum or opening allowing access to an interior surface of the piston. The disc valve is typically in a closed position that prevents injections or other incursions into the bag, thus preserving the integrity and sterility of the bag contents.

25 Claims, 2 Drawing Sheets

FLEXIBLE MULTI-USE CONTAINER, SYSTEM AND METHOD OF MANUFACTURE

This application claims priority under 35 U.S.C. §119(e) to U.S. Provisional Application No. 61/943,023, filed on Feb. 21, 2014, the disclosure of which is incorporated herein by reference in its entirety.

FIELD

The presently disclosed subject matter relates to a multi-use container for the storage and administration of solutions, and more particularly, to a combination multi-use, multi-compartment container and one-way dispensing valve assembly for aspirating or otherwise removing fluids from the container.

BACKGROUND

One of the most widely used methods of medical therapy involves the intravenous (IV) infusion of liquid medicaments and/or nutrients into the bloodstream of a patient. This is commonly referred to as intravenous infusion therapy and typically the entire contents of an IV container are infused into a patient during a single procedure. Conventional IV containers include IV bags or bottles which can contain the liquid to be infused into the patient.

When the IV container is a bag, a rigid, hollow, sharpened IV spike is typically pushed into the bag port to establish a pathway for fluid communication through which the liquid can flow out of the bag. The spike, in turn, is typically connected to or formed integrally with an inlet port of a small, elongated, transparent hollow container familiarly referred to as a "drip chamber," with the fluid pathway of the spike in fluid communication with the inlet port of the drip chamber. An IV line is typically connected to an outlet port (which usually is located below the inlet port) of the drip chamber. A flow control clamp (such as a roller clamp or other suitable flow regulating device) can be engaged with the IV line, and a medical technician can manipulate the flow control clamp to squeeze the IV line and thereby regulate fluid flow through the IV line. To establish a path for fluid communication from the IV container to the patient, a sharp needle is connected to the IV line to puncture the patient. Together, the drip chamber with outlet tube and clamp is referred to as an "IV set."

Typically, the bag or bottle is elevated above the patient to establish a positive pressure head to force the fluid that is within the bag or bottle through the drip chamber into the patient. Because the drip chamber is transparent, a medical technician can view the medicament as it passes (normally by dripping) through the drip chamber to aid the medical technician in establishing a predetermined flow rate of medicament into the patient as the medical technician adjusts the roller clamp on the IV line. This IV set can also be used with a pump or fluid delivery system. Conventional IV sets that utilize a needle and catheter can be problematic because they raise the risk of needle stick injuries and contamination of the IV fluid.

Conventional IV containers, including IV bags also are typically intended for a single use due to the risk of contamination of the IV fluid. Multi-dose administration of medication is typically performed using glass vials having elastomeric stoppers that require fluid to be withdrawn using a syringe and a needle. These systems also raise the risk of needle sticks and glass breakage. Furthermore, fluids in a glass vial are premixed and thus have shorter shelf life than unmixed medications.

SUMMARY

In view of the foregoing characteristics of and problems with conventional IV containers, the disclosed embodiments provide a multi-compartment, multi-use container that allows for drug reconstitution and safe access for multi-use applications. Multi-use applications can also be referred to as multi-dose applications that allow withdrawing medication for periodic administration to a single patient from a single container until the container is empty or until the need no longer exists for the bag contents. The terms multi-use container, multi-dose container multi-use bag, multi-dose bag and IV bag can be used interchangeably based on the intended use of the container. In one embodiment of the disclosed subject matter, the multi-dose container is a multi-compartment plastic bag having a one-way, needle free, aspiration valve. In accordance with the disclosed embodiments, the multi-compartment bag can separate one component, such as a drug, from another component, such as a diluent.

The disclosed embodiments include a multi-compartment plastic bag that can be segmented or partitioned into a plurality, e.g., two, three or more, chambers separated by at least one peelable seal. The peelable seals are rupturable so as to facilitate the mixing of the contents between the various chambers. For example, rupturing a peelable seal could allow the contents of the chambers to safely mix without exposure to the environment or being contacted by humans. A chamber can be larger than the other chamber(s) or each chamber can be of equal or substantially similar dimensions or volume. A first chamber, which can be the larger chamber, can contain a liquid diluent(s) while the other chamber(s) can contain an active pharmaceutical ingredient (API), which can be a dry powder, liquid, or gas. Another chamber can be empty and define or form a buffer space or region that separates the drug from a delivery set port.

The disclosed embodiments further include a valve structure that is hermetically sealed to a lower flange formed on the plastic bag to form a one-way outlet accessible with a luer tip syringe that does not have a needle. In accordance with an embodiment of the disclosed subject matter, the valve structure can include a piston in combination with a disc or disc valve. In this embodiment, the piston can have a slit septum or opening allowing access to an interior surface of the piston. Also, in this embodiment, the disc valve is typically in a closed position. This normally closed position prevents injections into the bag, thus preserving the integrity of the bag contents.

Thus, the exemplary valve structure can be used for aspirating fluid from a container such as an intravenous fluid bag. In one embodiment, the valve structure partially opens when the luer tip of a syringe is inserted into the slit septum. In this embodiment, the valve structure fully opens when the syringe plunger is pulled back, creating a negative pressure on the opening and the normally closed valve disc. In particular, when a syringe is attached to a lower portion of the valve structure and the syringe plunger is withdrawn, a negative pressure is created and increases the relative pressure forcing the disc to further flex away from a valve seat (shoulder). When the negative pressure created by the syringe plunger is released, the disc returns to its normally closed position with a top surface of the disc and the shoulder forming an annular seal. When a full or partially full syringe is attached to the dispensing valve assembly, it is difficult and/or impossible to empty the contents of the syringe into a container through the valve. Positive pressure applied by the syringe plunger will only contribute to a tighter seal between the top surface of the disc and the valve shoulder.

The disclosed valve structure and multi-dose container combination prevents fluid seepage if the bag is dropped or squeezed excessively. In most cases, positive pressure on the bag would open the normally closed disc valve. However, the addition of a slit septum adds an additional barrier to leakage. The slit septum also provides additional contamination protection by providing a surface that can easily be cleaned with an alcohol wipe.

Thus, the disclosed embodiments provide a one-way dispensing valve assembly for aspirating fluid, which allows for withdrawal of fluid from a container, but does not allow flow of fluid back into the same or different container. The disclosed subject matter also provides a one-way aspiration valve that prevents the introduction of contaminants and infectants back into the original receptacle, such as an IV bag. The exemplary one-way dispensing valve assembly for aspirating fluid can prevent alteration and dilution of the fluid in an original container by preventing the reintroduction of an unused portion of the fluid back into the original container. The disclosed embodiments further provide a one-way dispensing valve assembly for aspirating fluid into a syringe (without needle).

BRIEF DESCRIPTION OF THE DRAWINGS

The disclosed subject matter of the present application will now be described in more detail with reference to exemplary embodiments of the apparatus, system, and method, given by way of example, and with reference to the accompanying drawings, in which.

DETAILED DESCRIPTION OF EXEMPLARY EMBODIMENTS

This application incorporates by reference the entire disclosures of the following commonly assigned patents and patent applications: U.S. Pat. Nos. 5,944,709; 6,198,106; 6,165,161; 6,203,535; 5,910,138; 5,928,213; 6,468,377; 6,117,123; 6,846,305; 6,764,567; 6,996,951; U.S. Provisional Application No. 61/872,833; and U.S. Provisional Application No. 61/909,034.

Figure 1:
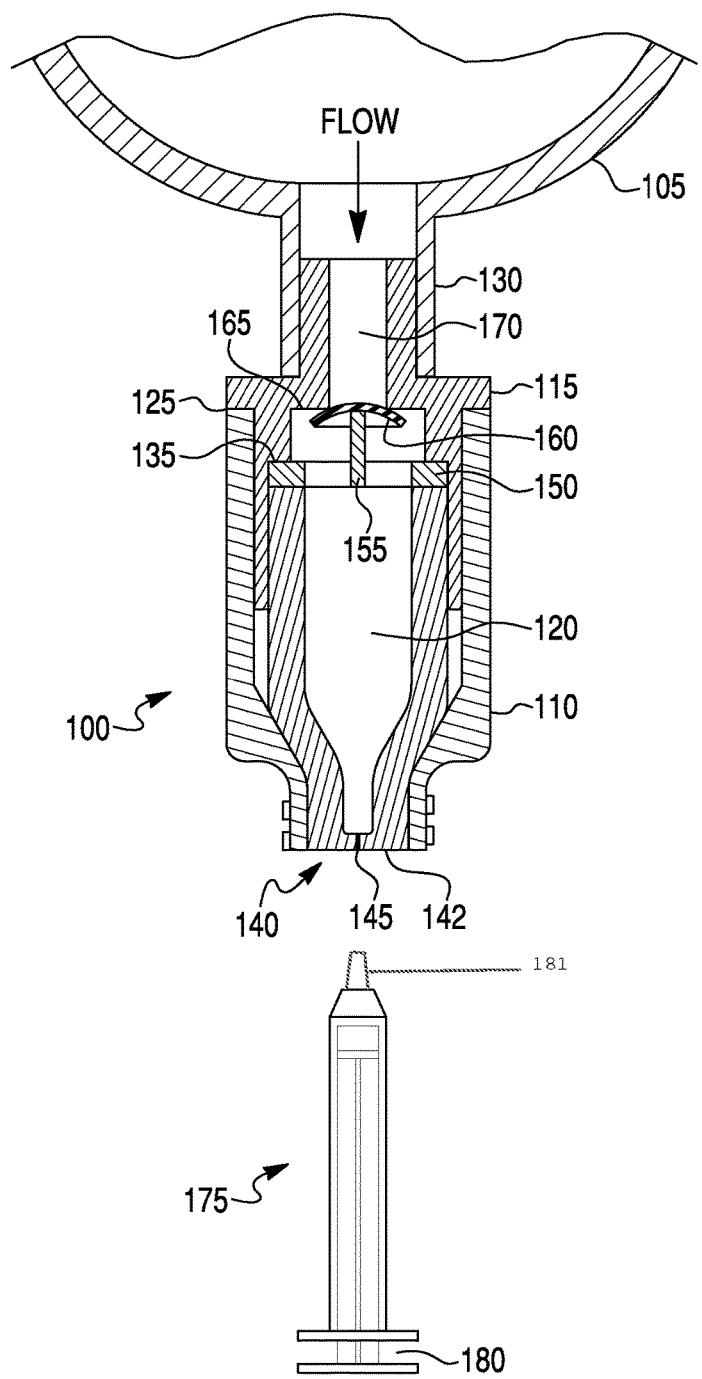
FIG. 1 is a cross-sectional view of a one-way, needle free, aspiration valve in communication with a lower portion of a multi-dose container in accordance with an embodiment of the disclosed subject matter.

FIG. 1 shows a cross-sectional view of an embodiment of a valve structure 100 in fluid communication with multi-dose container 105. The valve structure 100 of this embodiment is generally cylindrical in shape, however, it should be understood that the valve structure 100 can be any number of shapes including, but not limited to a square, rectangular, etc. The valve structure 100 allows one-way, multi-use access to the contents of the container 105 without the use of a needle. The valve structure 100 includes a housing 110 and a connector 115. The connector 115 includes a first shoulder 135 and a second shoulder 165. As shown in FIG. 1, a portion of the connector 115 is fitted within an internal surface (inner wall) of the housing 110 so that a first passageway 120 and a second passageway 170 are formed. The connector 115 can be held within the housing 110 through a variety of mechanisms, such as through friction fitting. Alternately, the connector 115 can be coupled to the housing 110 through a sonic weld formed at a welding point 125, or by a separate device such as a clamp or pin, etc. The connector 115 is configured to be in fluid communication with a bag port 130 formed on a lower surface of the container 105. This allows fluid communication to occur between an interior of the valve structure and the contents of the container. The disclosed embodiments also contemplate the connector 115 being formed integrally with the bag port 130. In this embodiment, the bag port 130 is formed as a portion of the valve structure 100.

FIG. 1 also shows a piston 140 formed within the first passageway 120. The piston 140 has a first end that terminates at a slit septum 142. As shown in FIG. 1, a slit 145 is formed through the slit septum 142 that allows access to the first passageway 120. A portion of an opposing end of the piston 140 can be in communication with an inner surface of the connector 115. FIG. 1 also shows a spacer 150 formed between an opposing end of the piston 140 and the first shoulder 135 of the connector 115. The spacer 150 also includes a rib portion 155 formed across opposing circumferential surfaces of the spacer 150. The exemplary spacer 150 of FIG. 1 has a generally circular (cylindrical) shape and the rib portion 155 is generally triangular in shape and extends in a direction parallel to a central axis of the opening of the spacer 150.

FIG. 1 also shows a resilient valve disc 160 that separates the first passageway 120 from the second passageway 170. The valve disc 160 can be made from a number of resilient materials, such as a silicone elastomer, in a variety of suitable thicknesses. As described above, the rib portion 155 is shown as a triangular base, but can be any shape that will accommodate a bottom surface of valve disc 160 and help provide a seal between a top surface of the valve disc 160 and the second shoulder 165 (also referred to as a valve seat 165). FIG. 1 also shows a syringe 175 having a plunger 180. The syringe can be configured such that its tip 181 can be inserted into the first passageway 120 via the slit 145 of the slit septum 142.

In the normally closed position, valve disc 160 is partially flexed by the rib portion 155 against the valve seat 165 to form an annular seal. During aspiration, the valve disc 160 is further flexed and separated from valve seat 165 by a drop in differential pressure of the first passageway 120 relative to the second passageway 170. This differential pressure or pressure drop can be realized by inserting the tip of the syringe 175 into the first passageway 120 and then pulling back the syringe plunger 180. As valve disc 160 is flexed away from valve seat 165, the annular seal is broken to permit fluid flow from the second passageway 170 to first passageway 120, typically in a downward or lateral direction. When the pulling action of the syringe is stopped, valve disc 160 returns to its original, normally closed position with the top surface of the disc 160 in contact with valve seat 165, thereby renewing the seal and preventing flow in either direction. Specifically, flow from the syringe 175 and from the first passageway 120 back into the bag 105 is prevented to avoid contamination of the remaining contents of the bag 105.

In one embodiment, the top of rib 155 is substantially co-planar with the valve seat 165. This spatial relationship creates a seal between the disc 160 and the valve seat 165 for a variety of disc thicknesses.

The slit 145 formed on the bottom surface 142 of the piston 140 is capable of receiving the luer tip of the syringe 175. When a luer tip 181 of the syringe 175 is inserted into the slit 145, the valve structure 100 is partially opened. The valve structure 100 fully opens when, as described above, the plunger 180 of the syringe 175 is pulled back creating a negative pressure within the first passageway 120 and thus opening the normally closed disc 160.

The disclosed valve closure combination, e.g., the disc 160 and the slit 145, prevents fluid seepage if the bag is dropped or squeezed excessively. Typically, positive pressure on the bag would open a normally closed disc, but the addition of a septum creates additional protection against leakage and adds an additional layer of contamination protection by providing a surface that can be easily cleaned with an alcohol wipe.

The piston 140 can be configured of relatively elastic material (elastic at least with respect to the housing 110 and the connector 115) such that when a reduced pressure exists in the first passageway 120, the piston 140 allows the spacer 150 and disc 160 to move downward against the elastic force of the piston 140 material to thus unseat the disc from the valve seat 165 and open the valve 100. When pressure is normalized between chambers 120 and 170, the elastic return force of the piston 140 allows the spacer 150 and disc 160 to return to the normally closed state where the disc 160 mates with the valve seat 165. Alternatively, a separate elastic or spring structure can be provided between the spacer and the piston 140 (or other location) to provide the elastic force for opening and closing the disc 160 relative to the valve seat 165.

Figure 2:
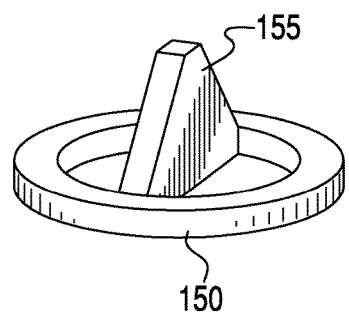
FIG. 2 is a perspective view of a spacer in accordance with an embodiment of the disclosed subject matter.

FIG. 2 shows a close-in view of the rib portion 155 and spacer 150. The embodiment of FIG. 2 shows the spacer 150 having a circular shape so that it can be held within the exemplary valve structure 100. In the embodiment of FIG. 2, the spacer 150 and rib portion 155 are formed so that the rib portion 155 is fitted or molded integrally within the spacer 150. It should be noted that the disclosed embodiments also contemplate other shapes and configurations for both the rib portion 155 and the spacer 150, depending on the geometry of the associated valve structures. The spacer 150 and valve disc 160 are shown as being separately formed structures. However, it is contemplated that the spacer and valve disc 160 can be formed as a unitary structure rather than as separate components. Also, the shape of the valve disc 160 could be changed depending upon the shape of the valve structure 100. In addition, it is contemplated that the rib portion 155 can be formed in various alternative configurations, such as a cone with various apertures, openings or windows running along the conically extending surface, as well as various other shapes that serve to space the valve disc 160 while permitting fluid to flow through the rib portion 155 and spacer 150.

Figure 3:
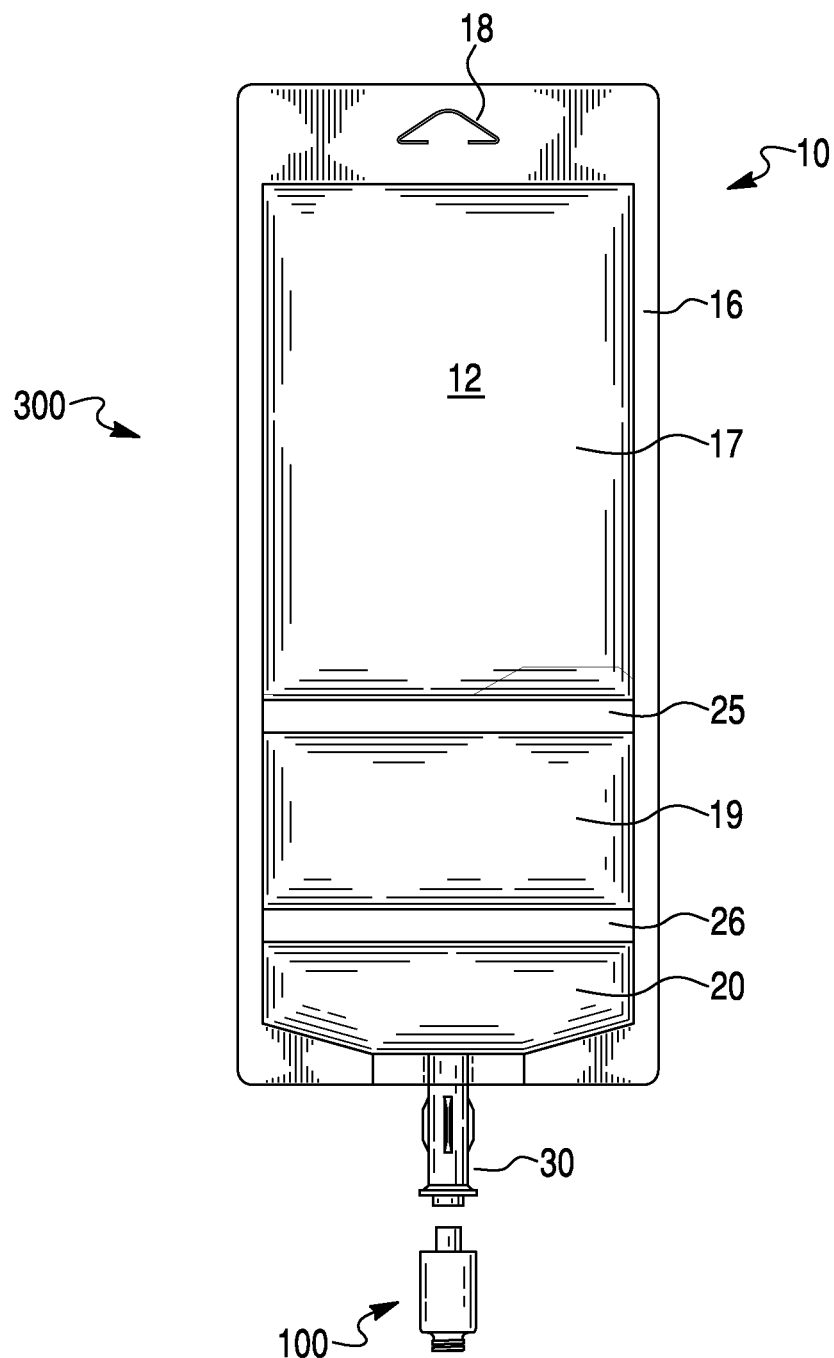
FIG. 3 is a perspective view of a multi-compartment bag and valve structure in accordance with an embodiment of the disclosed subject matter.

FIG. 3 shows a multi-compartment bag 300 that can be used with the valve structure 100 described above. The multi-compartment bag 300 can be formed from a generally planar front sheet 12 and an opposing generally planar back or rear sheet (not shown). The front sheet 12 and rear sheet can be constructed of a single layer of flexible material or multi-layer laminates of flexible material.

The front sheet 12 and rear sheet forming the container 300 can be provided separately and disposed opposing each other along a common plane. The sheets can then be sealed together along a common peripheral edge 16 with a permanent seal. The sealed common peripheral edge 16 extends around the entire periphery of the container 300 and cooperates with a first peelable seal 25 to form a first chamber 17. The peripheral seal may vary in configuration and width, and can be formed by heat sealing, vibration welding, etc. An opening 18 can be provided on a top surface of the container 300 which allows the container to be mounted, hung from, or otherwise attached to, for example, a support stand. Alternatively, the front sheet 12 and rear sheet (not shown) may be formed from a single film sheet which is folded-over and the edges sealed together by any known or later developed sealing process.

In the exemplary embodiment of FIG. 3, the bag 300 is partitioned into three separate chambers: a first or upper chamber 17; a second or intermediate chamber 19; and, a third or lower chamber 20, each of which can be sterile, depending on the intended application of the bag 300. The upper and intermediate chambers 17 and 19 are separated from one another by a first peelable seal 25, while the intermediate and lower chambers 19 and 20 are separated from one another by a second peelable seal 26. In other embodiments of the disclosed subject matter, a peelable seal can only be provided between the upper chamber 17 and the intermediate chamber 19. In these embodiments, the seal between the intermediate chamber 19 and the lower chamber 20 can be rupturable through the application of a hydraulic force caused by a user forcing the contents of the upper and intermediate chambers 17 and 19 into the lower chamber 20.

A "peelable" seal, as the term is used herein, is a seal which is sufficiently durable to allow normal handling of the container without inadvertent or unintentional rupturing of the seal (resulting in the contents of the compartments mixing unintentionally), while also allowing the seal to rupture easily when intended and desired. The seal is ruptured using hydraulic pressure applied by manipulating or squeezing the container/bag. Once the seal is intentionally ruptured, the contents from adjacent chambers 17 and 19 can be mixed together and eventually dispensed from the container. The peelable seal can be formed by partially melting together the polymeric material present in the adjoining interior faces of the front and back sheets. The seal is obtained by, for example, a heat sealing process wherein heat and pressure is applied to a localized area with varying times, temperatures, and pressures which will be described in greater detail below. Rupturing the peelable seal can allow the contents of the chambers to safely mix without exposure to the environment or being contacted by a human. It should also be understood that one chamber can be larger than the other chamber(s) or each chamber can be of equal of substantially similar dimensions or volume.

In one application for the container/bag 300, the upper compartment 17 is filled with a liquid diluent and the intermediate compartment 19 is filled with a medicament, such as an active pharmaceutical ingredient, or other nutritional or supplemental ingredient intended to be received intravenously or ingested by the user or patient and which can be provided in any form, including a liquid, gel, gas, or solid form. The lower compartment 20 can function as a security interface for an outlet port 30 and remains empty until the container is ready to be used. In this embodiment, the upper chamber 17 can contain a liquid diluent(s) while the intermediate chamber 19 can contain the medicament, active pharmaceutical ingredient (API), nutritional ingredient, or other supplemental ingredient, any of which can be either a dry powder, gel, solid or a liquid.

As shown in FIG. 3, the outlet port 30 extends downwardly and includes a nozzle configured to engage the valve structure 100. As described above, the syringe 180 (FIG. 1) is configured to be inserted into the bottom section of the valve structure 100 via the slit 145 (FIG. 1). In use, a medical professional can mix the contents of the upper chamber 17 and the intermediate chamber 19 hydraulic force to open the peelable seal allowing the contents of the upper and intermediate chambers 17 and 19 to mix. Continued fluid pressure opens the final seal allowing the mixture to enter chamber 20. In this manner, the contents of the container are ready to be dispensed.

As described earlier, when a luer tip of the syringe 175 (FIG. 1) is inserted into the slit 145 (FIG. 1), the valve structure 100 is partially opened. The valve structure 100 fully opens when, as described above, the plunger 180 (FIG. 1) of the syringe 175 (FIG. 1) is pulled back creating a negative pressure within the first passageway 120 and thereby opening the normally closed disc 160 (FIG. 1). In this condition, fluid will flow from bag 300 through first and second passageways 170 (FIG. 1) and 120 (FIG. 1) into both the first passageway 120 and syringe 175 (FIG. 1).

A method for aspirating a fluid from a multi-dose container is also disclosed, and can include: providing the container along with a one way valve located adjacent a septum; inserting a syringe into the septum of the one way valve, the syringe including a plunger and a housing and not including a needle; and withdrawing the plunger from the housing of the syringe to cause a negative pressure within the septum and thereby drawing fluid from the container into at least one of the septum and the syringe.

As describe above, the valve structure 100, the piston 140 and the spacer 150 of FIG. 1 can have a generally cylindrical shape. However, these components can be formed in other shapes, including a rectangular shape, a square shape, etc. The valve structure 100 and its components can be made of a variety of materials, including various plastics and elastomers. For example, the housing 110, the connector 115 and the spacer 155 can be formed from a hard plastic material, such as but not limited to polypropylene, polycarbonate and the like. The piston 140 can be formed from various materials, including but not limited to elastomers. In one embodiment, the piston 140 is formed of a resilient material having a relative hardness that is less than the relative hardness of the housing 110, the connector 115 and the spacer 155. The valve disc 160 can be made from a number of resilient materials, such as a silicone elastomer, in a variety of suitable thicknesses.

The slit 145 in the septum 142 can also have a variety of shapes. In the depicted embodiment, the slit 145 is shown as a straight line. However, it is possible for the slit 145 to be shaped as a cross, an arc, a sine wave, a star, an asterisk, or other shape. The slit 145 can be specially configured to match with the shape of a luer tip of the syringe 175. Moreover, if the luer tip of the syringe 175 is shaped as a cross, the slit 145 can also be formed as a cross to tightly seal with the luer tip when the syringe 175 is inserted in the septum 142. Additionally, the slit 145 could be replaced with a frangible hinged portion that partially tears away to allow the syringe 175 to be inserted into the septum 142, but remains attached at a hinge portion such that the frangible portion does not float away or become entrained in the fluid in the passageway 120. The slit 145 can extend from an area outside of the septum 142 all the way through the septum 142 to the first passageway 120 such that resiliency of the material that makes up the septum 142 causes the slit 145 to remain closed to separate the first passageway 120 from an area outside the valve 100. Alternatively, the slit 145 can extend only partially through the septum. In this case, it will be necessary to forceably rupture the slit 145 with the syringe 175 (or other device) to allow the syringe access to the first passageway 120.

The septum 142 described above is not limited to a slit piston, but can also be configured to function as a needleless, luer-activated valve. One such example is the type of septum disclosed in U.S. Pat. No. 5,439,451 to Collinson, which teaches castellations on top, thereby allowing the fluid to flow around the piston instead of through the piston. Another alternate embodiment could be a piston having a slit and internal cannula as disclosed in U.S. Pat. No. 6,113,068, wherein the syringe moves the piston inward thereby exposing the cannula via the slit, which would allow the fluid to pass through the cannula and out of the valve.

In the above description and the claims that follow, words descriptive of orientation (upper, bottom, etc.) are provided to clarify the disclosed subject matter. They refer to the orientation shown in the drawings. However, it should be understood that the disclosed valve may be used in any orientation.

Since the disclosed subject matter is subject to modifications and variations, it is intended that the foregoing description and the accompanying drawings shall be interpreted as illustrative of only one form of the disclosed embodiments, whose scope is to be measured by the following claims. In addition, the disclosure and teachings in all of the above-described related art patent documents are hereby incorporated in their entireties by reference.

The invention claimed is:

1. An aspiration valve device comprising:
   a housing body having a first passageway therethrough;
   a connector body having a second passageway therethrough, the connector body including a first seat and a valve seat, at least a portion of the connector body formed within the first passageway;
   a piston body formed within the first passageway, the piston body including a septum disposed at a first end of the piston body; and
   a flexible valve disc having a top surface engaging the valve seat of the connector body, the flexible valve disc positioned between the piston body and the valve seat of the connector body,
   wherein the housing body, the connector body and the flexible valve disc form a one-way valve, and
   wherein the top surface of the disc forms an annular seal with the valve seat of the connector body.

2. The aspiration valve device according to claim 1, including a spacer provided between the first seat of the connector body and the piston body.

3. The aspiration valve device according to claim 1, wherein the piston body is configured such that a fluid pressure drop in the first passageway increases a relative pressure in the second passageway such that the disc is flexed away from the valve seat and allows fluid from the second passageway into the first passageway.

4. The aspiration valve device according to claim 1, wherein the housing body and the connector body are formed as a single unitary structure.

5. The aspiration valve device according to claim 1, wherein the septum of the piston body includes a slit defined therein.

6. The aspiration valve device according to claim 1, further comprising:
   a flexible bag configured to be removably attached to the connector body.

7. The aspiration valve device according to claim 6, wherein the flexible bag includes multiple chambers separated by peelable seals such that the contents of the flexible bag can be selectively mixed at a desired time.

8. The aspiration valve device according to claim 7, further comprising:
a syringe configured to mate with the septum in the piston body.

9. The aspiration valve device according to claim 6, further comprising:
a syringe configured to mate with the septum in the piston body.

10. The aspiration valve device according to claim 1, further comprising:
a syringe configured to mate with the septum in the piston body.

11. The aspiration valve device according to claim 1, wherein the piston body is made from an elastic material and the housing body is made from a material that is relatively inelastic as compared to the elastic material of the piston body.

12. The aspiration valve device according to claim 11, wherein the connector body and the housing body are a single integral structure.

13. The aspiration valve device according to claim 1, further comprising:
a spacer located between the piston body and the valve disc, the spacer including at least one opening that allows fluid flow to pass therethrough.

14. The aspiration valve device according to claim 13, wherein the piston body includes a cylinder made from a relatively elastic material, and the spacer is located at an end of the piston body and configured to maintain the valve disc in a first closed state when a first pressure exists in the first passageway and to allow the valve disc to move to a second open state when a second pressure lower than the first pressure exists in the first passageway.

15. An aspiration valve device comprising:
a housing defining a first passageway and a second passageway, the housing including a connector having a valve seat which defines an opening at an end of the second passageway and a shoulder located in the first passageway, and the housing including an outlet opening at an end of the first passageway located at an outlet end of the housing;
a valve structure engaging the valve seat and located between the first passageway and the second passageway; and
an elastomeric structure located within the first passageway and opposing the shoulder of the connector, the elastomeric structure being relatively more elastic than the housing, the elastomeric structure configured to bias the valve structure towards a closed state where the valve structure does not permit fluid to flow between the first passageway and second passageway, the elastomeric structure also including a port structure located adjacent the outlet end of the housing and configured to be connected to a source of negative pressure,
wherein the valve structure is located between the valve seat and the elastomeric structure.

16. The aspiration valve device of claim 15, further comprising a spacer structure located between the shoulder of the connector and an axial end of the elastomeric structure,
wherein the elastomeric structure is configured as a cylinder to define a flow path therethrough,
wherein the valve structure and spacer are located at a first end of the cylinder, and
wherein the port structure is configured as a septum located at a second opposite end of the cylinder.

17. An aspiration kit comprising:
a housing body having a first passageway, a second passageway, and a shoulder defined by the housing body and located in the first passageway;
a valve engaging a valve seat defined by the housing body and separating the first passageway from the second passageway;
a piston body located in the first passageway and having an axial end opposing the shoulder of the housing body, wherein the shoulder is located between the valve and the piston body, the piston body also including a septum disposed at a first end of the piston body; and
a syringe having a luer tip with no needle and configured to mate with the septum.

18. The kit of claim 17, further comprising:
a flexible dose container.

19. The kit of claim 17, wherein the septum of the piston body includes a slit defined therein.

20. An aspiration valve device comprising:
a housing body having a first passageway therethrough;
a connector body having a second passageway therethrough, the connector body including a first seat and a valve seat, at least a portion of the connector body formed within the first passageway;
a piston body formed within the first passageway and opposing the first seat, the piston body including a septum disposed at a first end of the piston body, wherein the first seat is located between the valve seat and the piston body;
a spacer located between and engaging the first seat and an axial end of the piston body;
and
a flexible valve disc having a top surface, the flexible valve disc located between the spacer and the valve seat,
wherein the housing body, the connector body and the flexible valve disc form a one-way valve, wherein the top surface of the disc forms an annular seal with the valve seat of the connector body.

21. The aspiration valve device according to claim 20, wherein the piston body is configured such that a fluid pressure drop in the first passageway increases a relative pressure in the second passageway such that the disc is flexed away from the valve seat and allows fluid from the second passageway into the first passageway.

22. The aspiration valve device according to claim 20, wherein the housing body and the connector body are formed as a single unitary structure.

23. The aspiration valve device according to claim 20, wherein the septum of the piston body includes a slit defined therein.

24. The aspiration valve device according to claim 20, further comprising a flexible bag configured to be removably attached to the connector body.

25. The aspiration valve device according to claim 20, wherein the spacer includes at least one opening that allows fluid flow to pass therethrough.

* * * * *